United States Patent [19]  
Castle et al.

[11] 4,423,740  
[45] Jan. 3, 1984

[54] SLIT CATHETER METHOD FOR MEASURING INTERSTITIAL PRESSURE

[75] Inventors: G. S. Peter Castle; Cecil H. Rorabeck, both of London, Canada

[73] Assignee: Howmedica, Inc., New York, N.Y.

[21] Appl. No.: 249,314

[22] Filed: Mar. 31, 1981

[51] Int. Cl.³ .............................................. A61B 5/00
[52] U.S. Cl. .................................................. 128/748
[58] Field of Search ........................ 128/634, 673–675, 128/692, 748, 242–244, 348–350, 214.4, 347, 328, 772, DIG. 9

[56] References Cited

U.S. PATENT DOCUMENTS

| | | | |
|---|---|---|---|
| Re. 27,310 | 1/1968 | Hakin | 128/350 R |
| 2,042,900 | 6/1936 | James | 128/243 X |
| 3,169,529 | 2/1965 | Koenig | 128/351 |
| 3,717,151 | 2/1973 | Collett | 128/347 |
| 3,815,608 | 6/1974 | Spinosa | 128/349 R |
| 3,866,599 | 2/1975 | Johnson | 128/634 |
| 3,896,804 | 7/1975 | Ekbladh et al. | 128/215 |
| 4,192,319 | 3/1980 | Hargens | 128/748 |
| 4,209,023 | 6/1980 | Layton | 128/748 |

Primary Examiner—Lee S. Cohen  
Attorney, Agent, or Firm—Charles J. Knuth; Kittie A. Murray; Lawrence C. Akers

[57] ABSTRACT

An interstitial tissue pressure measuring device comprising a cannula and a catheter, the catheter being adapted to pass through the cannula and the distal end of the catheter being provided with a plurality of longitudinal slits defining a plurality of petals between them. When the cannula is emplaced in an interstitial tissue site and the catheter is passed through the emplaced cannula into the tissue, the petals facilitate measurement of pressure by a pressure-sensing device at the proximal end of the catheter.

4 Claims, 7 Drawing Figures

U.S. Patent    Jan. 3, 1984    4,423,740
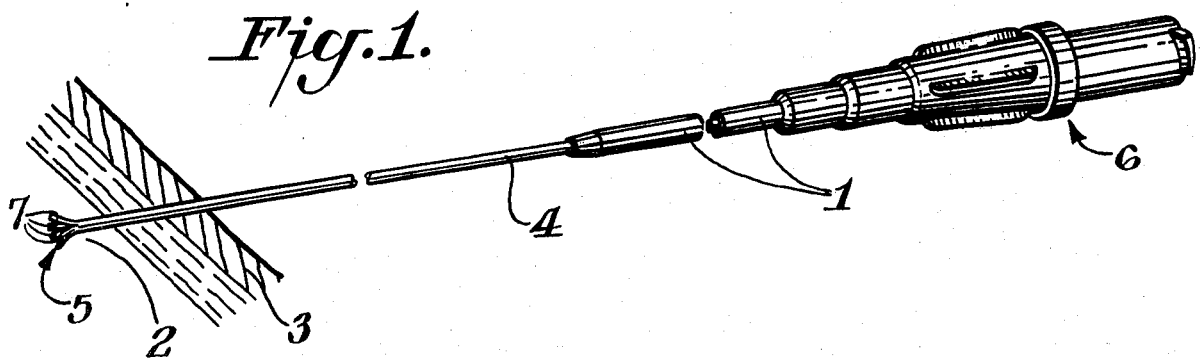
Fig.1.
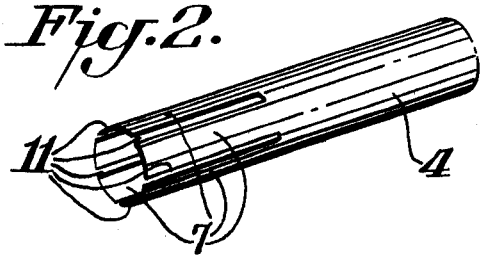
Fig.2.
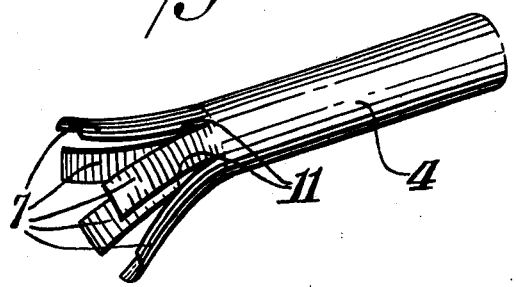
Fig.3.
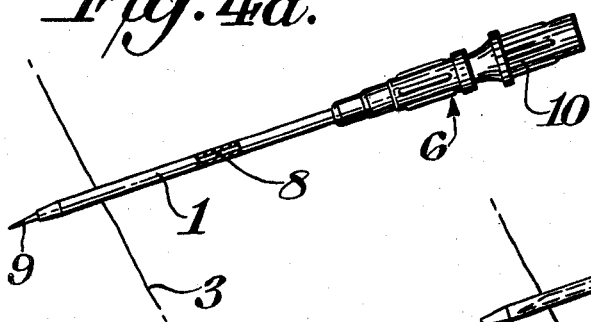
Fig.4a.
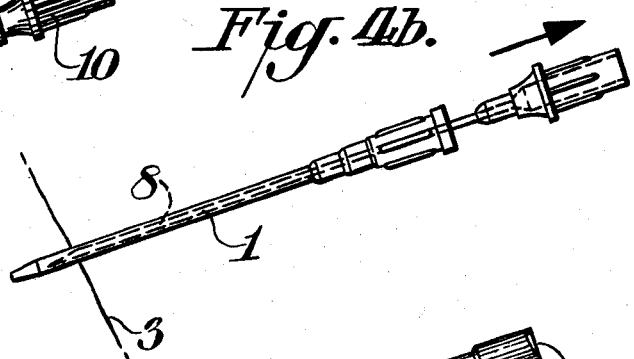
Fig.4b.
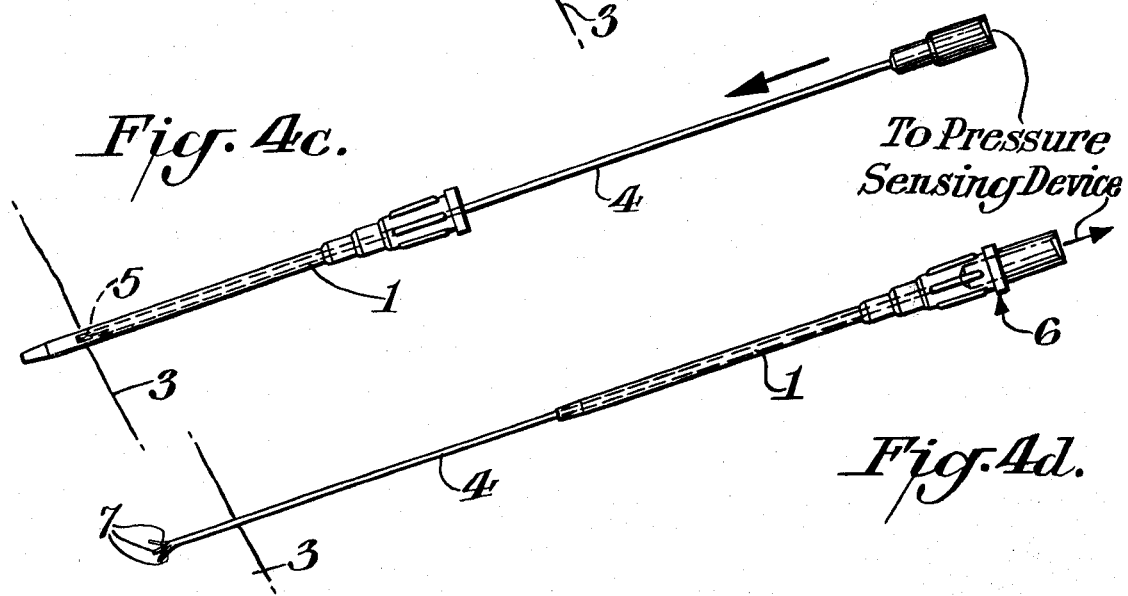
Fig.4c.
Fig.4d.
To Pressure Sensing Device

SLIT CATHETER METHOD FOR MEASURING INTERSTITIAL PRESSURE

BACKGROUND OF THE INVENTION

The present invention relates to interstitial tissue pressure measuring devices.

Interstitial tissue pressure measurement is a useful diagnostic adjunct in the prevention of the sequelae of acute compartmental syndromes. After surgery or accidental injury, pressure in tissues confined within a fascial compartment often increases to a level which causes discomfort and even permanent muscle and nerve damage. If this pressure build-up is diagnosed in its initial stage, a fasciotomy can be performed to remove the excess fluid causing the harmful pressure thereby preventing permanent tissue damage.

A number of techniques are known for measuring interstitial tissue pressure. U.S. Pat. No. 4,209,023 discloses a tissue pressure measuring device utilizing a simple needle connected to a pressure sensing means. This technique requires continuous or intermittent perfusion which limits the reproducibility of measurements and possibly aggravates compartmental syndrome. A wick catheter pressure sensing probe disclosed in U.S. Pat. No. 4,192,319 gives reliable results but is difficult to assemble and insert interstitially without undue trauma to the patient. Moreover, the wick catheter technique suffers from the disadvantage of a fragile structure, which could lead to in situ breakage. In addition it is difficult to manufacture in a reproducible manner and loses its accuracy after four hours with continuous monitoring.

SUMMARY OF THE INVENTION

Accordingly, it is an object of this invention to provide a method for measuring interstitial tissue pressure which is reliable, safe and easy to perform.

A further object of the present invention is to provide an interstitial pressure measuring method suitable for both instantaneous and continuous pressure measurements.

These and other objects of the invention are achieved with a novel apparatus for measuring interstitial tissue pressure comprising a cannula and a cylindrical catheter for reception of a physiologically compatible fluid, the proximal end of the catheter being attached to a pressure sensing device and the distal end of the catheter being provided with a plurality of longitudinal slits defining a plurality of petals between them, the petals being capable of expanding radially to form an obtuse angle with the adjacent catheter wall when inserted interstitially, said expanded petals providing an unobstructed opening to the catheter and access to an enlarged hydrostatic pool for pressure measurement.

BRIEF DESCRIPTION OF THE DRAWINGS

FIG. 1 is a pictorial view of the catheter and cannula of the present invention in elevation shown emplaced interstitially;

FIG. 2 is an enlarged pictorial view of the distal end of the catheter of FIG. 1 in non-expanded form;

FIG. 3 is an enlarged pictorial view of the distal portion of the catheter of FIG. 1 in radially expanded form; and FIG. 4 shows the steps comprising the method of using the present invention wherein FIG. 4a shows the cannula being inserted subcutaneously and interstitially by means of a guiding needle therein concentrically confined;

FIG. 4b shows the needle being extracted from the interstitial site leaving the cannula in situ;

FIG. 4c shows the catheter being pushed through said cannula into the tissue mass; and FIG. 4d shows the cannula withdrawn from the tissue and interlocked at the proximal end of the catheter leaving the distal end of the catheter emplaced and radially expanded in situ.

DETAILED DESCRIPTION OF THE INVENTION

The invention will be described in detail with reference to a preferred embodiment thereof, which is separable combination of a cannula and a polyethylene catheter the distal end thereof being provided with longitudinal slits defining a plurality of petals between them. Reference to this embodiment does not limit the scope of the invention, which is limited only by the scope of the claims.

A preferred embodiment of the present invention, i.e. a cannula and a slit catheter therein confined, is shown in FIG. 1. Cannula (1) shown in FIG. 1 after retraction from the tissue is a tube of length sufficient to span the distance between the desired interstitial site (2) and the overlying skin (3). Cannula (1) is preferably a plastic tube but may be a needle of the break-away type or fitted with longitudinal slits.

Catheter (4) is tubing composed of a plastic material such as polyethylene of length sufficient to extend from said interstitial site (2) to a distance outside said overlying skin (3) where it may be taped to the skin or otherwise secured. The length of said catheter will generally be about 20 to 35 cm with about 25 cm preferred. The catheter is filled before interstitial insertion with a physiologically compatible fluid such as sterile saline.

In a novel aspect of the present invention, the distal end (5) of said catheter is comprised of a plurality of slits generally from 2 to 8 extending longitudinally for a distance of about 2 mm to 8 mm from the open end thereof and defining a plurality of petals between them. Preferably the present invention comprises 5 slits extending about 4 mm in length.

FIG. 2 shows the slits (11) defining petals (7) at the distal end of the catheter.

FIG. 3 shows the petals (7) in radially expanded position. In the preferred embodiment of the invention the petals form an obtuse angle of about 160 to 170 degrees with the adjacent catheter wall. The catheter may be prestressed before or after being slit to position the petals at this angle. The expanded petals keep interfering material from the distal end of the implanted catheter and thus provide an uninterrupted conduit of fluid for transmission of pressure from the interstitial site at the distal end to an attached pressure sensing device at the proximal end thereof.

In the preferred embodiment of the invention, the inner diameter of the cannula is sufficient to accomodate the petals of the catheter in their expanded position.

In an alternative embodiment, the inner diameter of the cannula accomodates the catheter snugly so that the petals are restrained by the cannula and remain essentially parallel to the longitudinal axis of the catheter tubing while concentrically confined in the cannula but expand radially when released from confinement.

In the preferred embodiment of the invention, as shown in FIG. 1, the proximal ends of the catheter and said cannula are provided with interlocking means (6) whereby the cannula (1) is maintained circumferentially about the proximal length of the catheter (2) after withdrawl of the cannula from the tissue. One example of interlocking means is adaptors shaped to snugly fit one inside the other in a male-female relationship. A preferred embodiment comprises plastic adaptors but metal adaptors are also suitable.

The interlocking means on the catheter is also adapted to receive concurrently with the cannula a suitable pressure sensing device.

The novel interstitial pressure measuring device is used in the following manner. With reference to FIG. 4a, a cannula (1) of about 5 cm length is inserted through the overlying skin, sub-cutaneous tissue and deep fascia into the desired interstitial site by means of a guiding needle (8) therein snugly confined, the acutely beveled end (9) of the needle protruding from the distal end of the cannula and the proximal end of the needle (10) being interlocked with the proximal end (6) of the cannula. The point of the needle is withdrawn to a position inside the cannula and the cannula is further pushed using blunt insertion to the desired tissue site. The needle is removed, leaving the cannula in situ as shown in FIG. 4b.

The proximal end of the catheter is attached to an assembly of a pressure transducer and its associated pressure reading device. The catheter-pressure measuring assembly is flushed with physiologically compatible fluid, thus freeing the system of air bubbles and is pressure-calibrated. As shown in FIG. 4c, the slit distal end (5) of the catheter is introduced into the cannula, fed through the cannula (1) and finally implanted in the tissue. The cannula (1) is retracted from the tissue circumferentially along the catheter (4) to the interlocking means located at the proximal end of the catheter (6) as shown in FIG. 4d.

The catheter extending from the tissue site is strapped to the skin. Pressure readings may be instantaneous or may be monitored and/or recorded over a period of time.

In an alternative method of use, the catheter is delivered to the desired interstitial site within a needle which is subsequently withdrawn leaving the catheter in situ. The needle in this method is preferably of the breakaway type or is slotted longitudinally to facilitate its removal from the catheter without interference with the attached pressure-sensing device.

The foregoing detailed description is for clearness of understanding only, and no unnecessary limitations should be understood therefrom.

Other variations of the present invention will be apparent to those skilled in the art and are considered to be within the scope of the invention.

We claim:

1. A method for measuring interstitial tissue pressure comprising:

inserting a cannula into said interstitial tissue;

passing an unobstructed catheter having a distal end and a proximal end and having an inner wall and an outer wall through said inserted cannula into said interstitial tissue, said catheter being filled with a physiologically compatible fluid and the distal end thereof being provided with a plurality of longitudinal slits defining a plurality of petals between them;

withdrawing said cannula from said interstitial tissue leaving the distal end of said catheter in situ with said petals forming an obtuse angle with the adjacent inner catheter wall; and reading said pressure on a pressure sensing device at the proximal end of said catheter.

2. A method of claim 1 wherein the number of said slits and said petals is five and the length of said slits is about 4 mm.

3. A method of claim 2 wherein the obtuse angle formed by said petals with the adjacent inner catheter wall is about 160 to 170 degrees.

4. A method of claim 1 wherein the obtuse angle formed by said petals with the adjacent inner catheter wall is about 160 to 170 degrees.

* * * * *